US00PP13571P2

(12) United States Plant Patent
Bergman

(10) Patent No.: US PP13,571 P2
(45) Date of Patent: Feb. 18, 2003

(54) AZALEA PLANT NAMED 'VIBRATION'

(75) Inventor: Wendy R. Bergman, Lehigh Acres, FL (US)

(73) Assignee: Yoder Brothers, Inc., Barberton, OH (US)

( * ) Notice: Subject to any disclaimer, the term of this patent is extended or adjusted under 35 U.S.C. 154(b) by 0 days.

(21) Appl. No.: 10/099,270

(22) Filed: Mar. 15, 2002

(51) Int. Cl.[7] ..... A01H 5/00
(52) U.S. Cl. ..... Plt./238
(58) Field of Search ..... Plt./238

*Primary Examiner*—Kent L. Bell

(74) *Attorney, Agent, or Firm*—C. A. Whealy

(57) ABSTRACT

A new and distinct cultivar of Azalea plant named 'Vibration', characterized by its dark green-colored leaves that do not abscise during the cooling and forcing periods; upright and outwardly spreading plant habit; freely branching habit; usually about three to four lateral branches develop after pinching; uniform and freely flowering habit; rapid flowering response; numerous, large and showy white-colored flowers with random red purple-colored flecks and spots; semi-double to double flower form; excellent post-production longevity with plants maintaining good flower substance for about four weeks in an interior environment; and very low incidence of infection with Cylindrocladium in inoculated trials.

1 Drawing Sheet

BOTANICAL CLASSIFICATION/CULTIVAR DESIGNATION

*Rhododendron hybrida* 'Vibration'.

BACKGROUND OF THE INVENTION

The present Invention relates to a new and distinct cultivar of Azalea, botanically known as *Rhododendron hybrida,* an evergreen greenhouse-forcing type Azalea, and hereinafter referred to by the name 'Vibration'.

The new Azalea is a product of a planned breeding program conducted by the Inventor in Alva, Fla. The objective of the breeding program is to create new Azalea varieties having uniform plant habit, profuse and uniform flowering response, dark green foliage, good foliage retention during the cooling and forcing periods, resistance to Cylindrocladium, and excellent postproduction longevity.

The new Azalea originated from a cross-pollination made by the Inventor in June, 1993, in Alva, Fla., of a proprietary Azalea selection identified as code number YB-0903, not patented, as the female, or seed, parent with a proprietary Azalea selection identified as code number YB-0327, not patented, as the male, or pollen, parent. The new Azalea was discovered and selected by the Inventor as a flowering plant within the progeny of the stated cross in a controlled environment in Alva, Fla., in January, 1996. The selection of this plant was based on its large and showy white-colored flowers with random red purple-colored flecks and spots, semi-double to double flower form, uniform flowering response, good foliage retention, and excellent postproduction longevity.

Asexual reproduction of the new Azalea by terminal cuttings taken in a controlled environment in Alva, Fla. since May, 1996, has shown that the unique features of this new Azalea are stable and reproduced true to type in successive generations.

SUMMARY OF THE INVENTION

The new Azalea has not been observed under all possible environmental conditions. The phenotype may vary somewhat with variations in environment such as temperature, daylength and/or light intensity without, however, any variance in genotype.

The following traits have been repeatedly observed and are determined to be the unique characteristics of 'Vibration'. These characteristics in combination distinguish 'Vibration' as a new and distinct cultivar:

1. Dark green-colored leaves that do not abscise during the cooling and forcing periods.
2. Upright and outwardly spreading plant habit.
3. Freely branching habit; usually about three to four lateral branches develop after pinching.
4. Uniform and freely flowering habit.
5. Rapid flowering response; plants begin flowering about 23 days after cooling treatment.
6. Numerous, large and showy white-colored flowers with random red purple-colored flecks and spots.
7. Semi-double to double flower form.
8. Excellent postproduction longevity with plants maintaining good flower substance for about four weeks in an interior environment.
9. Very low incidence of infection with Cylindrocladium in inoculated trials.

In side-by-side comparisons conducted in Alva, Fla., plants of the new Azalea differed from plants of the female parent, the selection YB-0903, in the following characteristics:

1. Plants of the new Azalea were larger and grew faster than plants of the selection YB-0903.
2. Plants of the new Azalea had better foliage retention under stress conditions than plants of the selection YB-0903.
3. Flowers of plants of the new Azalea were white in color with random red purple-colored flecks and spots whereas flowers of plants of the selection YB-0903 were white in color without flecks and spots.

In side-by-side comparisons conducted in Alva, Fla., plants of the new Azalea differed from plants of the male parent, the selection YB-0327, in the following characteristics:

1. Plants of the new Azalea were more uniform in plant habit and not as vigorous as plants of the selection YB-0327.

2. Flowers of plants of the new Azalea were white in color with random red purple-colored flecks and spots whereas flowers of plants of the selection YB-0327 were dark pink in color without flecks or spots.

Plants of the new Azalea can be compared to the plants of the cultivar 'YB 871 Remembrance', disclosed in U.S. Plant Pat. No. 9,132. However, in side-by-side comparisons conducted in Alva, Fla., plants of the new Azalea differed from plants of the cultivar 'YB 871 Remembrance' in the following characteristics:

1. Plants of the new Azalea had larger leaves than plants of the cultivar 'YB 871 remembrance'.

2. Plants of the new Azalea had larger flowers than plants of the cultivar 'YB 871 Remembrance'.

3. Flowers of plants of the new Azalea were white in color with random red purple-colored flecks and spots whereas flowers of plants of the cultivar 'YB 871 Remembrance' were pink in color without flecks or spots.

BRIEF DESCRIPTION OF THE PHOTOGRAPHS

The accompanying colored photographs illustrate the overall appearance of the new Azalea. These photographs show the colors as true as it is reasonably possible to obtain in colored reproductions of this type. Colors in the photographs may differ slightly from the color values cited in the detailed botanical description, which accurately describe the colors of the new Azalea.

The photograph at the top of the sheet comprises a side perspective view of a typical flowering plant of 'Vibration'.

The photograph at the bottom of the sheet is a close-up view of typical flowers of 'Vibration'.

DETAILED BOTANICAL DESCRIPTION

The aforementioned photographs and following observations and measurements describe plants grown in Alva, Fla. with three plants per 15-cm containers, in a polypropylene-covered shade house during the late winter and early spring under commercial production conditions. During the productio of the plants, day temperatures ranged from 13 to 38° C. and night temperatures ranged from 0 to 26° C. Plants were pinched at planting, pinched a second time about 12 weeks later, and then pinched a third time about 12 weeks after the second pinch. After sufficient flower bud development, plants were cooled at 3 to 5° C. for six weeks to break flower bud dormancy. Plants were subsequently forced into flower under commercial production conditions in a polyethylene-covered greenhouse. Plants used for the photographs and description were about 12 months from planting rooted young plants.

In the following description, color references are made to The Royal Horticultural Society Colour Chart, 1995 Edition, except where general terms of ordinary dictionary significance are used.

Botanical classification: *Rhododendron hybrida* 'Vibration'.

Commercial classification: Evergreen greenhouse-forcing type Azalea.

Parentage:

*Female or seed parent.*—Proprietary selection of *Rhododendron hybrida* identified as code number YB-0903, not patented.

*Male or pollen parent.*—Proprietary selection of *Rhododendron hybrida* identified as code number YB-0327, not patented.

Propagation:

*Type.*—By terminal vegetative cuttings.

*Time to initiate roots.*—Summer: About 35 days at temperaturs of 24° C. Winter: About 42 days at temperatures of 24° C.

*Time to develop roots.*—Summer: About 63 days at temperatures of 24° C. Winter: About 77 days at temperatures of 24° C.

*Root description.*—Fine, fibrous, and white in color.

*Rooting habit.*—Freely branching.

Plant description:

*Plant form and growth habit.*—Perennial, evergreen; upright and outwardly spreading plant habit; broad inverted triangle; moderately vigorous growth habit. Densely foliated. Freely flowering; numerous flowers per plant.

*Branching habit.*—Freely branching; about three to five lateral branches develop after pinching (removal of terminal apex).

*Plant height, soil level to top of flowers.*—About 23.5 cm.

*Plant diameter, area of spread.*—About 47.5 cm.

*Lateral branch description.*—Length: About 25 cm. Diameter at base: About 5 mm. Texture: Young: Pubescent, fine brown hairs. Mature: Woody; pubescent, fine brown hairs. Color: Young: 144A. Mature: 164A to 165A.

*Foliage description.*—Arrangement: Alternate, single. Foliage retention: Very good foliage retention on plants of the new Azalea that have been in a box for six weeks during the cooling treatment. Length: About 5.3 cm. Width: About 3 cm. Shape: Mostly obovate. Apex: Cuspidate to mucronate. Base: Cuneate. Margin: Entire. Venation pattern: Pinnate. Texture, upper and lower surfaces: Leathery, tough, durable; pubescent. Luster, upper and lower surfaces; Slightly glossy. Color: Young and mature foliage, upper surface: Much darker green than 147A. Young and mature foliage, lower surface: Close to 147B. Venation, upper surface: Main veins, close to 146A; lateral veins, same as lamina. Venation, lower surface: Main veins, close to 146B; lateral veins, same as lamina. Petiole: Length: About 7 mm. Diameter: About 2 mm. Texture, upper surface: Smooth, glabrous. Texture, lower surface: Pubescent. Color: Upper surface: Close to 144A. Lower surface: Close to 144A to 144B.

Flower description:

*Natural flowering season.*—Spring after sufficient cool period. If forced, plants typically flower about 23 days after a six-week cooling treatment. Flowers persistent.

*Flower arrangement.*—Flowers arranged singly at terminals with usually about three to four flowers per apex; freely flowering. Flowers face upward and outward.

*Flower appearance.*—Large semi-double to double flower form; white-colored flowers with random purple-colored flecks and spots.

*Fragrance.*—Very faint, sweet.

*Flower diameter.*—Large, about 9.5 cm.

*Flower depth.*—About 5 cm.

*Postproduction longevity.*—Under interior conditions, plants maintain good flower substance for about four weeks.

*Flower bud* (*before showing color*).—Rate of opening: About three to seven days depending on temperatures. Length: About 1.5 cm. Diameter: About 8 mm. Shape: Ovoid. Texture: Covered with fine brown pubescence. Color: Close to 144A to 144B.

*Petals.*—Arrangement: Semi-double to double flower form; single whorl of five fused petals surrounding a whorl of stamens mostly transformed into petal-like structures. Length: About 5.5 cm. Width: About 4.2 cm. Shape: Beyond fused base, roughly orbicular with rounded apex. Margin: Entire, undulate. Texture, upper and lower surfaces: Smooth, satiny. Color: When opening, upper and lower surfaces: White, close to 155D, with random red purple, closest to 64C, flecks and spots; towards margin and base, overlain with 144A to 144B. Fully opened, upper and lower surfaces: White, close to 155D, with random red purple, closest to 64C, flecks and spots.

*Sepals.*—Arrangement/appearance: Single whorl of five sepals fused towards base; leaf-like. Length: About 1.5 cm. Width: About 6 mm. Shape: Roughly deltoid. Apex: Acute. Margin: Entire. Texture, upper and lower surfaces: Fine white pubescence. Color, upper and lower surfaces: 144A to 146A.

*Peduncles.*—Length: About 1.5 cm. Diameter: About 2.5 mm. Angle: Upright to about 30° from vertical. Strength: Flexible; strong. Texture: Pubescent. Color: 144A to 146A.

*Reproductive organs.*—Androecium: Stamens transformed into petal-like structures; occasionally stamens are not transformed. True stamens: Quantity of stamens: None to five per flower. Filament length: About 2.3 cm. Filament diameter: Less than 1 mm. Filament color: Close to 155D. Anther size: About 2 mm by 1.5 mm. Anther shape: Oblong. Anther color: Close to 163A. Amount of pollen: None observed. Transformed stamens: Appearance: None to five per flower; irregular in size, shape and quantity per flower. Length: About 4.5 cm. Width: About 2.4 cm. Shape: Roughly spatulate with rounded apex. Margin: Entire, undulate. Texture, upper and lower surfaces: Smooth, satiny. Color: When opening, upper and lower surfaces: White, close to 155D, with random red purple, closest to 64C, flecks and spots; towards margin and base, overlain with 144A to 144B. Fully opened, upper and lower surfaces: White, close to 155D, with random red purple, closest to 64C, flecks and spots. Gynoecium: Quantity of pistils: One per flower. Pistil length: About 3.4 cm. Style length: About 3.1 mm. Style diameter: Less than 1 mm. Style color: Close to 155D. Stigma diameter: About 1 mm. Stigma shape: Rounded. Stigma color: Close to 144C. Ovary color: Close to 146A; heavily whiskered.

*Seed.*—Seed production has not been observed.

Weather/temperature tolerance: Plants of the new Azalea have been observed to be very tolerant to rain and wind. Plants of the new Azalea have been observed to tolerate temperatures from 0 to 38° C.

Disease/pest resistance: In inoculated trials that were conducted in Alva, Fla. during the summers of 1999 and 2001, plants of the new Azalea have been observed to be very resistant to infection by Cylindrocladium. Plants have not been observed to be resistant to pests common to Azaleas.

It is claimed:

1. A new and distinct Azalea plant named 'Vibration', as illustrated and described.

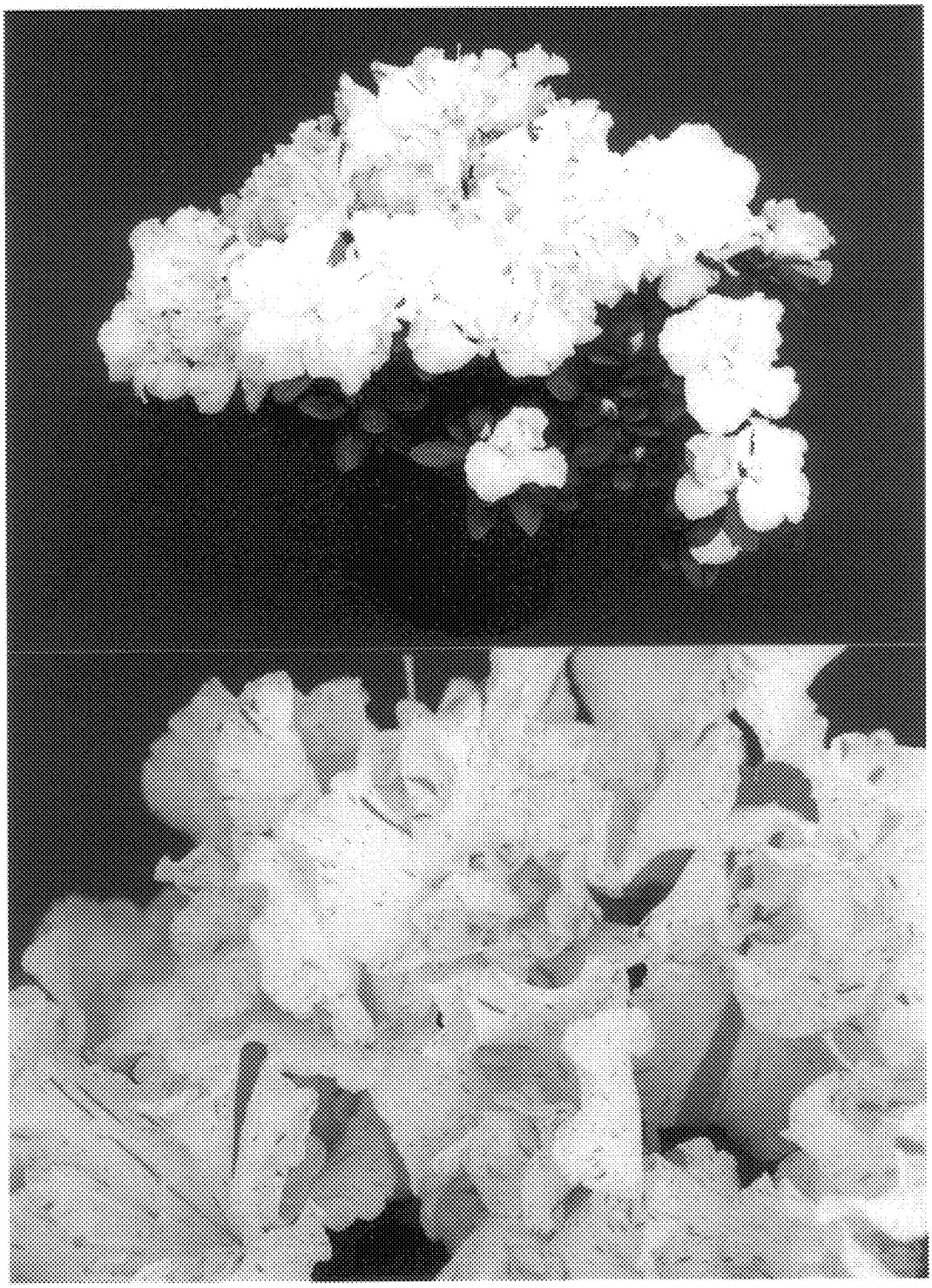

* * * * *